(12) United States Patent
Ci (10) Patent No.: US 10,485,832 B2
(45) Date of Patent: Nov. 26, 2019

(54) CHINESE HERBAL ORAL PASTE FOR CONDITIONING QI DEPRESSION CONSTITUTION AND PROCESSING METHOD THEREFOR

(71) Applicant: Zhonghua Ci, Beijing (CN)

(72) Inventor: Zhonghua Ci, Beijing (CN)

( * ) Notice: Subject to any disclaimer, the term of this patent is extended or adjusted under 35 U.S.C. 154(b) by 0 days.

(21) Appl. No.: 15/967,095

(22) Filed: Apr. 30, 2018

(65) Prior Publication Data
US 2019/0192595 A1 Jun. 27, 2019

(30) Foreign Application Priority Data
Dec. 26, 2017 (CN) .......................... 2017 1 1429362

(51) Int. Cl.
| | | |
|---|---|---|
| *A61K 36/00* | (2006.01) |
| *A61K 36/233* | (2006.01) |
| *A61K 36/484* | (2006.01) |
| *A61K 36/236* | (2006.01) |
| *A61K 36/752* | (2006.01) |
| *A61K 36/534* | (2006.01) |
| *A61K 36/738* | (2006.01) |
| *A61K 36/535* | (2006.01) |
| *A61K 36/8945* | (2006.01) |
| *A61K 36/9064* | (2006.01) |
| *A61K 35/586* | (2015.01) |
| *A61K 47/26* | (2006.01) |
| *A61K 45/06* | (2006.01) |
| *A61P 25/24* | (2006.01) |
| *A61K 9/00* | (2006.01) |
| *A61K 36/65* | (2006.01) |
| *A61K 9/107* | (2006.01) |

(52) U.S. Cl.
CPC .......... *A61K 36/233* (2013.01); *A61K 9/0053* (2013.01); *A61K 9/107* (2013.01); *A61K 35/586* (2013.01); *A61K 36/236* (2013.01); *A61K 36/484* (2013.01); *A61K 36/534* (2013.01); *A61K 36/535* (2013.01); *A61K 36/65* (2013.01); *A61K 36/738* (2013.01); *A61K 36/752* (2013.01); *A61K 36/8945* (2013.01); *A61K 36/9064* (2013.01); *A61K 45/06* (2013.01); *A61K 47/26* (2013.01); *A61P 25/24* (2018.01); *A61K 2236/13* (2013.01); *A61K 2236/51* (2013.01)

(58) Field of Classification Search
None
See application file for complete search history.

(56) References Cited

PUBLICATIONS

No reference is cited.*

\* cited by examiner

*Primary Examiner* — Qiuwen Mi
(74) *Attorney, Agent, or Firm* — Novick, Kim & Lee, PLLC; Allen Xue (57) ABSTRACT

The present application discloses a Chinese herbal oral paste for conditioning qi depression constitution. The Chinese herbal oral paste includes the following components: Chinese thorowax root, debark peony root, licorice, Sichuan lovage rhizome, dried tangerine peel, orange fruit, nutgrass galingale rhizome, mint, fuling, perilla leaf, largehead atractylodes rhizome, fruit of caoguo, common aucklandia root, chinaberry fruit, lychee seed, finger citron, citron fruit, rose flower, citrus aurantium L, silktree albizia bark, nardostachys root, grassleaf sweetflag rhizome, heterophylly falsestarwort root, Chinese yam, white hyacinth bean, dendrobium, turmeric root tuber, donkey-hide gelatin, turtle shell gelatin, tortoise-plastron gelatin, and xylitol. The Chinese herbal oral paste of the present disclosure has a higher drug concentration and good taste, is particularly suitable for health preserving in winter and conditioning the qi depression constitution, will not create negative effects to the human body at all, and is capable of achieving certain efficacy of strengthening physical health.

20 Claims, 1 Drawing Sheet

CHINESE HERBAL ORAL PASTE FOR CONDITIONING QI DEPRESSION CONSTITUTION AND PROCESSING METHOD THEREFOR

TECHNICAL FIELD

The present disclosure relates to the field of health foods, and particularly to a Chinese herbal oral paste for conditioning qi depression constitution and a processing method therefor.

BACKGROUND

In *Classification and Determination of Constitution in Traditional Chinese Medicine*, the China Association of Chinese Medicine classifies body constitutions of the human body into nine types, including yin-yang harmony constitution, yang deficiency constitution, yin deficiency constitution, qi deficiency constitution, phlegm-dampness constitution, damp-heat constitution, qi depression constitution, blood stasis constitution, and allergic constitution, most of which belong to sub-healthy states.

The qi depression constitution is a constitution state formed due to long-term poor mood and qi-movement stagnation, with the main manifestation of introverted and unstable personality, depression and fragility, and being sensitive and suspicious. Such constitution state is common in the young and middle-aged, female predominated, mostly being solitary and introverted in personality, prone to be sentimental, and narrow minded. The diseases of people with the qi depression constitution mainly come on the liver, together with the heart, stomach, large intestine, and small intestine. It will easily result in damages to the emotion and diet, unsmooth qi-movement, such as depression disease, insomnia, globus hysteriocus, and panic. It is found in modern researches that such constitution tends to develop tumors. The regulation and treatment should be regulating the emotion and dredging the qi-movement.

Such sub-healthy constitution as qi depression constitution generally belongs to depression constitution. People with the qi depression constitution should pay attention to mentality regulation, mind regulation, and nature cultivation in daily life, maintaining good psychological balance, and doing more physical exercises. Since the qi depression occurs first, and stasis is the basis, dredging the qi-movement is the treatment principle. The drug forms commonly used in the traditional Chinese medicine are decoctions and Chinese patent medicine such as pills and the like. Decoctions usually have relatively good efficacy, but the administration thereof is complicated, and the taste thereof is poor. If the decoctions need to be prepared for a long time, it is difficult for a patient to keep taking the decoctions. Moreover, the efficacy of the pills is relatively poor.

It is mentioned in the *Inner Canon of the Yellow Emperor* that "the superior physician prevents illness, the mediocre physician attends to impending illness, and the inferior physician treats actual illness", wherein the phrase "prevent illness" means taking corresponding measures to prevent the occurrence and development of diseases. The body constitution determines the health of people and susceptibility to diseases. It is believed in the traditional Chinese medicine that since the human beings live in the natural world, physiological functions of the human body usually change with seasons, that is, "correspondence between man and nature". Winter is the season when the human body "stores energies", thus appropriate nourishment can enhance the constitution, ward off diseases and strengthen the body, and prolong life, that is, conditioning in winter or nourishing in winter commonly mentioned in the traditional Chinese medicine. For the sub-healthy population with qi depression constitution, a solid oral paste with a higher drug concentration and good taste, and being convenient to carry more meets requirements of modern people.

SUMMARY

A main object of the present disclosure is to provide a Chinese herbal nourishing product suitable for conditioning in winter so as to treat qi depression constitution.

In order to achieve the above object, according to one aspect of the present disclosure, there is provided a Chinese herbal oral paste for conditioning qi depression constitution.

The Chinese herbal oral paste for conditioning qi depression constitution according to the present disclosure includes the following components in parts by weight: 9-18 parts of Chinese thorowax root, 5-15 parts of debark peony root, 2-11 parts of licorice, 2-10 parts of Sichuan lovage rhizome, 4-16 parts of dried tangerine peel, 5-16 parts of orange fruit, 3-8 parts of nutgrass galingale rhizome, 5-15 parts of mint, 5-16 parts of fuling, 4-14 parts of perilla leaf, 5-16 parts of largehead atractylodes rhizome, 12-28 parts of fruit of caoguo, 5-15 parts of common aucklandia root, 5-16 parts of chinaberry fruit, 6-18 parts of lychee seed, 5-14 parts of finger citron, 5-16 parts of citron fruit, 6-16 parts of rose flower, 3-10 parts of citrus aurantium L, 4-15 parts of silktree albizia bark, 5-16 parts of nardostachys root, 4-9 parts of grassleaf sweetflag rhizome, 8-22 parts of heterophylly falsestarwort root, 5-15 parts of Chinese yam, 5-15 parts of white hyacinth bean, 4-17 parts of dendrobium, 6-18 parts of turmeric root tuber, 10-30 parts of donkey-hide gelatin, 5-15 parts of turtle shell gelatin, 5-15 parts of tortoise-plastron gelatin, and 20-40 parts of xylitol.

Furthermore, the Chinese herbal oral paste for conditioning qi depression constitution according to the present disclosure includes the following components in parts by weight: 9-15 parts of Chinese thorowax root, 7-13 parts of debark peony root, 4-8 parts of licorice, 4-8 parts of Sichuan lovage rhizome, 7-13 parts of dried tangerine peel, 7-13 parts of orange fruit, 5-7 parts of nutgrass galingale rhizome, 7-13 parts of mint, 7-13 parts of fuling, 7-13 parts of perilla leaf, 7-13 parts of largehead atractylodes rhizome, 16-24 parts of fruit of caoguo, 7-13 parts of common aucklandia root, 8-13 parts of chinaberry fruit, 9-15 parts of lychee seed, 7-12 parts of finger citron, 7-13 parts of citron fruit, 8-13 parts of rose flower, 5-7 parts of citrus aurantium L, 7-13 parts of silktree albizia bark, 7-13 parts of nardostachys root, 5-7 parts of grassleaf sweetflag rhizome, 11-19 parts of heterophylly falsestarwort root, 7-13 parts of Chinese yam, 7-13 parts of white hyacinth bean, 7-13 parts of dendrobium, 9-15 parts of turmeric root tuber, 15-25 parts of donkey-hide gelatin, 7-13 parts of turtle shell gelatin, 7-13 parts of tortoise-plastron gelatin, and 25-35 parts of xylitol.

Furthermore, the Chinese herbal oral paste for conditioning qi depression constitution according to the present disclosure includes the following components in parts by weight: 12 parts of Chinese thorowax root, 10 parts of debark peony root, 6 parts of licorice, 6 parts of Sichuan lovage rhizome, 10 parts of dried tangerine peel, 10 parts of orange fruit, 6 parts of nutgrass galingale rhizome, 10 parts of mint, 10 parts of fuling, 10 parts of perilla leaf, 10 parts of largehead atractylodes rhizome, 20 parts of fruit of caoguo, 10 parts of common aucklandia root, 10 parts of chinaberry fruit, 12 parts of lychee seed, 10 parts of finger citron, 10 parts of citron fruit, 10 parts of rose flower, 6 parts of citrus aurantium L, 10 parts of silktree albizia bark, 10 parts of nardostachys root, 6 parts of grassleaf sweetflag rhizome, 15 parts of heterophylly falsestarwort root, 10 parts of Chinese yam, 10 parts of white hyacinth bean, 10 parts of dendrobium, 12 parts of turmeric root tuber, 20 parts of donkey-hide gelatin, 10 parts of turtle shell gelatin, 10 parts of tortoise-plastron gelatin, and 30 parts of xylitol.

In order to achieve the above object, according to the other aspect of the present disclosure, there is a processing method for a Chinese herbal oral paste for conditioning qi depression constitution.

The processing method for a Chinese herbal oral paste for conditioning qi depression constitution according to the present disclosure includes the following steps in sequence: preparation of materials, soaking, decoction, concentration, and collecting an oral paste.

Furthermore, the step of preparation of materials is: measuring raw materials of formula ratio according to composition of the Chinese herbal oral paste, and washing raw materials, except turtle shell gelatin, tortoise-plastron gelatin, donkey-hide gelatin, and xylitol, for subsequent use.

Furthermore, the soaking step is: soaking the cleaned raw materials with 8-10 folds of water for 8-15 h, with the water over the raw materials by 10-20 cm.

Furthermore, the decoction step is: decocting the soaked drug materials over flame, firstly boiling the drug materials with high heat to sufficiently expand, then boiling the drug materials with low heat for 1-2 hours of decoction, then filtering drug juice with gauze, then soaking filtered dregs of decoction with clear water and decocting the soaked dregs of decoction with low heat for 1 hour, thus repeating 2-4 times, then combining the filtered drug juice, and squeezing and filtering the dregs to obtain squeezed juice; combining decoction juice with the squeezed juice, followed by static settlement for 2 h, and filtering, to obtain a supernatant liquid for subsequent use.

Furthermore, the concentration step is: boiling and skimming the supernatant liquid resulted in the decoction step, followed by stirring while decocting and concentrating with low heat, until the drug liquid does not disperse when being dropped on paper, to obtain a vegetarian paste.

Furthermore, the step of collecting an oral paste is: pouring xylitol, melted turtle shell gelatin, tortoise-plastron gelatin and donkey-hide gelatin into the vegetarian paste respectively, stirring them continuously with a shovel while cooking them slowly with low heat, until the juice coagulates into beads when dropped into clear water and does not disperse, then canning the resulted oral paste.

The melting step is: smashing lumps of turtle shell gelatin, tortoise-plastron gelatin and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

The Chinese herbal oral paste of the present disclosure has a higher drug concentration and good taste, is particularly suitable for health preserving in winter and conditioning the qi depression constitution, will not create negative effects or harm to the human body at all, and is capable of achieving certain efficacy of strengthening physical health.

BRIEF DESCRIPTION OF THE DRAWINGS

The accompanying drawing, which constitutes a part of the present application, is used to provide a further understanding of the present disclosure, so that other features, objects, and advantages of the present application become more obvious. The illustrative drawings for embodiments of the present disclosure and the description thereof are used to explain the present disclosure, rather than constitute an improper limitation on the present disclosure. In the drawing.

DETAILED DESCRIPTION OF THE EMBODIMENTS

In order to enable a person skilled in the art to better understand the solutions of the present application, the technical solutions of the embodiments of the present disclosure will be described clearly and completely below with reference to the accompanying drawing of the embodiments of the present application. Apparently, the embodiments described are merely for some of the embodiments of the present application, rather than all of the embodiments. All the other embodiments that are obtained by a person skilled in the art without inventive effort on the basis of the embodiments of the present application shall be covered by the protection scope of the present application.

In addition, the term "comprise" and any variant thereof are intended to cover non-exclusive inclusion, for example, a product comprising a series of raw materials or a method comprising a series of steps is not necessarily limited to the raw materials or the steps listed clearly, but can include other steps or raw materials that are not clearly listed or are inherent to the method and product.

It should be noted that the embodiments of the present application and the features of the embodiments can be combined with each other if there is no conflict. The present application will be described in detail below in combination with the embodiments.

The present disclosure provides a Chinese herbal oral paste for conditioning qi depression constitution, including the following components: Chinese thorowax root, debark peony root, licorice, Sichuan lovage rhizome, dried tangerine peel, orange fruit, nutgrass galingale rhizome, mint, fuling, perilla leaf, largehead atractylodes rhizome, fruit of caoguo, common aucklandia root, chinaberry fruit, lychee seed, finger citron, citron fruit, rose flower, citrus aurantium L, silktree albizia bark, nardostachys root, grassleaf sweetflag rhizome, heterophylly falsestarwort root, Chinese yam, white hyacinth bean, dendrobium, turmeric root tuber, donkey-hide gelatin, turtle shell gelatin, tortoise-plastron gelatin, and xylitol.

Chinese thorowax root is acrid and bitter in flavor and slightly cold in nature, acts on liver, gallbladder, and lung, reconciles superficies and interior, soothes liver and resolves depression, invigorates yang and descending qi, allays fever and prevents malaria, and is used for cold fever, alternating episodes of chills and fever, distending pain in chest and hypochondrium, irregular menstruation, uterine prolapse, and rectocele.

Debark peony root is bitter and sour in flavor and slightly cold in nature, acts on liver and spleen, soothes liver and relieves pain, replenishes blood and regulates menstruation, astringes yin and resists sweating, and is used for headache and vertigo, hypochondriac pain, stomachache, four-limb stiffness, blood-deficiency etiolation, irregular menstruation, spontaneous perspiration, and night sweating.

Licorice is sweet in flavor and neutral in nature, acts on heart, lung, spleen, and stomach, supplements spleen and tonifies qi, removes heat and toxic matters, eliminates phlegm and relieves cough, relieves spasm and alleviates pain, moderates various drugs, and is used for weakness of spleen and stomach, lassitude and asthenia, palpitation and short of breath, cough with excessive phlegm, abdominal distention, four-limb spasm and pain, carbuncle, and alleviation of drug toxicity and intensity.

Sichuan lovage rhizome is acrid in flavor and warm in nature, acts on liver and gallbladder, promotes the circulation of qi and resolves depression, dispels wind and dries dampness, invigorates blood circulation to stop pain, is used for wind-coldness headache and vertigo, hypochondriac pain and stomachache, arthritis and cramps, amenorrhea, dystocia, postpartum obstruction and pain, ulcer and skin and external diseases, and is used for irregular menstruation, amenorrhea and dysmenorrhea, abdominal mass pain, prickling in chest and hypochondrium, traumatic gall, headache, and arthralgia due to wind-dampness.

Dried tangerine peel is bitter and acrid in flavor and warm in nature, acts on lung and spleen, regulates qi and tonifies spleen, dries dampness and resolves phlegm, and is used for abdominal fullness and distention, reduced appetite and vomiting, and cough with excessive phlegm.

Orange fruit is bitter, acrid, and sour in flavor, and slightly cold in nature, acts on spleen and stomach, regulates qi and the middle energizer, removes stagnation and flatulence, and is used for distending pain in chest and qi stagnation, distention and pain, indigestion, phlegm-fluid retention and congestion, and flagging of internal organs.

Nutgrass galingale rhizome is acrid, slightly bitter, and slightly sweet in flavor and neutral in nature, acts on liver, spleen, and triple energizer meridian, soothes liver and resolves depression, regulates qi and the middle energizer, regulates menstruation and relieves pain, and is used for liver depression and qi stagnation, distending pain in chest and hypochondrium, hernia pain, breast tenderness, qi stagnation of spleen and stomach, abdominal fullness and stuffy feeling in chest, distention and fullness pain, irregular menstruation, and amenorrhea and algomenorrhea.

Mint is acrid in flavor and cool in nature, acts on lung and liver, dispels wind and heat, clears and disinhibits the head and eyes, relieves sore throat and promotes eruption, soothes the liver and promotes the circulation of qi, and is used for common cold due to wind-heat, headache, swollen sore throat, dyspepsia and flatulence, aphtha, toothache, furuncle, urticarial, beginning of warm diseases, rubella pruritus, liver depression and qi stagnation, chest distress and hypochondriac pain.

Fuling is sweet and light in flavor and neutral in nature, acts on heart, lung, spleen, and kidney, alleviates water retention and clears dampness, tonifies spleen, calms the mind, and is used for edema and scanty urine, phlegm and fluid retention and dizziness and palpitation, reduced spleen-deficiency appetite, loose stool and diarrhea, uneasiness, and palpitation to insomnia.

Perilla leaf is acrid in flavor and slightly warm in nature, and non-toxic, acts on spleen and lung, relieves exterior syndrome by diaphoresis, promotes the circulation of qi to regulate the middle energizer, and is used for wind-cold syndromes, qi stagnation in spleen and stomach, chest distress, vomiting, and vomiting of pregnancy.

Largehead atractylodes rhizome is bitter and sweet in flavor and warm in nature, acts on spleen and stomach, tonifies spleen and supplements qi, dries dampness and alleviates water retention, constrains sweating, prevents miscarriage, and is used for reduced spleen-deficiency appetite, abdominal distension diarrhea, phlegm and fluid retention and palpitation, edema, spontaneous perspiration, and fetal upset.

Fruit of caoguo is acrid in flavor and warm in nature, acts on spleen and stomach, dries dampness and tonifies spleen, warms stomach to stop vomiting, and is used for internal obstruction of cold and dampness, abdominal fullness and distention and crymodynia, belching circulation in the wrong direction, and poor appetite.

Common aucklandia root is acrid and bitter in flavor and warm in nature, acts on spleen, large intestine, and sanjiao, promotes the circulation of qi, stops pain, tonifies spleen, promotes digestion, and is used for qi circulation and pain alleviation, regulation of middle energizer and stagnation removal; hypochondriac distension, abdominal distention, vomiting and diarrhea, dysentery with tenesmus, swelling pain in chest and gastral cavity, diarrhea with tenesmus, indigestion, poor appetite, middle qi insufficiency, sudden hearing loss, snake and insect bites, and toothache.

Chinaberry fruit is bitter in flavor and cold in nature, and slightly toxic, acts on liver, small intestine, and bladder, soothes liver and promotes the circulation of qi to stop pain, expels parasites, and is used for chest and dypochondrium abdominal distention, colic, and abdominal pain due to parasitic infestation.

Lychee seed is sweet and slightly bitter in flavor and warm in nature, acts on liver and kidney, promotes the circulation of qi and removes stasis, eliminates cold to stop pain, and is used for cold abdominal colic stomachache and testicular swelling and pain.

Finger citron is acrid, bitter, and sour in flavor, and warm in nature, acts on liver, spleen, stomach, and lung, soothes liver and regulates qi, harmonizes stomach to relieve pain, dries dampness and eliminates phlegm, and is used for qi-stagnation in liver and stomach, distending pain in chest and hypochondrium, stomach distention and fullness, reduced appetite and vomiting, and cough with excessive phlegm.

Citron fruit is acrid, bitter, and sour in flavor and warm in nature, acts on liver, spleen, and lung, soothes liver and regulates qi, regulates the middle energizer, and eliminates phlegm, and is used for treatment of qi-stagnation in liver and stomach, distending pain in chest and hypochondrium, abdominal distention and fullness, vomiting and eructation, and excessive phlegm and cough.

Rose flower is sweet and slight bitter in flavor and warm in nature, acts on liver, spleen, and stomach, promotes qi and blood circulation, treats wind arthralgia, dispels fatigue and stops pain, and is used for hypermenorrhea, leukorrhea with reddish discharge and enteritis, bowel complaint, intestinal haemorrhage, etc.

Seville orange flower is slightly bitter and sour in flavor and slightly cold in nature, promotes the circulation of qi to regulate the middle energizer, promotes the digestion, and eliminates phlegm, and is used for depression and distending pain in chest and abdomen, indigestion, phlegm-fluid retention, rectocele, liver soothing, stomach harmonizing, qi regulation, stuffiness distress in the chest, abdominal distention, vomiting, and reduced appetite.

Silktree albizia bark is sweet in flavor and neutral in nature, acts on heart and liver, calms mind and resolves depression, invigorates blood circulation to resolve carbuncle, and is used for treatment of uneasiness, dejection, insomnia, inside and outside carbuncle, and traumatic injury.

Nardostachys root is acrid and sweet in flavor and warm in nature, acts on spleen and stomach, regulates qi and stops pain, resolves depression and refreshes spleen, eliminates dampness and relieves swelling upon external application, and is used for abdominal fullness and distention, poor appetite, vomiting, toothache and beriberi pyogenic infections upon external application.

Grassleaf sweetflag rhizome is acrid and bitter in flavor and warm in nature, acts on heart and stomach, resolves dampness and stimulates appetite, induces resuscitation and eliminates phlegm, refreshes spirit and develops intelligence, regulates circulation of qi, invigorates circulation of blood, relieves heat, eliminates dampness, and is used for fullness and distending pain in the chest and upper abdomen and anorexia, anorectic dysentery, unconsciousness and epilepsy, amnesia and hearing loss, epilepsy, coma due to blocking of the respiratory system, pyreticosis and unconsciousness, amnesia, deafness with stagnation, depression in heart and chest, stomachache, bellyache, wind-cold-dampness arthralgia, ulcer and pyogenic infection, and traumatic injury.

Heterophylly falsestarwort root is sweet and slightly bitter in flavor and neutral in nature, acts on spleen and lung, replenishes qi to tonify spleen, generates body fluid and moistens lung, and is used for spleen-deficiency body tiredness, poor appetite, weakness after illness, qi and yin insufficiency, spontaneous perspiration and mouth thirst, and lung-dryness dry cough.

Chinese yam is sweet in flavor, neutral in nature, and non-toxic, acts on spleen, lung, and kidney, strengthens spleen and stomach, nourishes lung qi, tonifies kidney essence, nourishes physical health, renders good hearing and eyesight and delays senility upon long administration, and is used for reduced spleen-deficiency appetite, loose stool diarrhea, lung-deficiency asthma, gonobolia and frequent urination, and yin-deficiency consumptive thirst.

White hyacinth bean is sweet in flavor and slightly warm in nature, acts on spleen and stomach, tonifies spleen and resolves dampness, regulates the middle energizer and relieves summer heat, and is used for spleen and stomach weakness, poor appetite, loose stool, leukorrhagia, diarrhoea caused by summer dampness, and oppression in the chest and abdominal distension.

Dendrobium is sweet flavor and slightly cold in nature, acts on stomach and kidney, benefits stomach and generates body fluid, nourishes yin and clears away heat, and is used for febrile disease and body fluid impairment, mouth dryness and polydipsia, lack of stomach yin, reduced appetite and vomiturition, persistent deficiency-heat after illness, yin-deficiency fire excess, steaming bone consumptive fever, blurred vision, and motor impairment of muscles and bones.

Turmeric root tuber is acrid, bitter, and cold, acts on liver, heart, and lung, invigorates blood circulation to stop pain, promotes the circulation of qi to resolve depression, clears away the heart fire and cools blood, benefits gallbladder and removes jaundice, and is used for prickling in chest and hypochondrium, chest obstruction and cardiac pain, amenorrhea and dysmenorrhea, breast tenderness, pyreticosis and unconsciousness, epilepsy and delirium, blood-heat haematemesis, and jaundice and dark urine.

Donkey-hide gelatin is sweet in flavor and neutral in nature, acts on lung, liver, and kidney, replenishes blood and nourishes yin, moistens dryness, stops bleeding, and is used for blood-deficiency etiolation, vertigo and palpitation, dysphoria insomnia, and lung dryness cough.

Turtle shell gelatin is sweet and salty in flavor and slightly cold in nature, acts on liver, lung, and kidney, nourishes yin and allays fever, resolves hard lump, and is used for yin-deficiency hectic fever, consumptive disease and hemoptysis, chronic malaria, malaria with abdominal mass, hemorrhoids gall, and blood-deficiency amenorrhea.

Tortoise-plastron gelatin is sweet and salty in flavor and neutral in nature, nourishes yin, replenishes blood, stops bleeding, and is used for yin-deficiency blood depletion, consumptive heat and steaming bone, hematemesis, bleeding from five sense organs or subcutaneous tissue, dysphoria with smothery sensation and palpitation, kidney-deficiency backache, impotent feet and knees, metrorrhagia and metrostaxis, and leucorrhoea.

People with the qi depression constitution are mostly physically emaciated or slightly overweight, pale and dark or chlorotic in complexion, usually quick-tempered and irritable, emotional, or melancholy, distressed in chest and uncomfortable, with frequent signing, reddish tongue, white tongue fur, and stringy pulse. The attacked will have distending pain in chest and hypochondrium or scurrying; or breast and underbelly swelling pain, irregular menstruation, dysmenorrhea; or obstruction in throat as if there were foreign matters; or gall in neck; or stomach distention swelling pain, acid dip spitting, hiccup eructation; or abdominal pain borborygmus, discomforting evacuation; or qi ascending counterflow, headache dizziness, sudden faint and haematemesis. The qi depression occurs first, and stasis is the basis, therefore, dredging the qi movement is the principle for recuperating people with the qi depression constitution. The Chinese herbal oral paste of the present disclosure regulates qi and resolves depression, warms the middle energizer and harmonizes stomach, soothes liver qi, nourishes heart yin, replenishes liver blood to calm mind, regulates and invigorates the qi movement, and promotes the circulation of qi to resolve stagnation. For the qi depression constitution, various drugs are used to enable the qi movement to be smooth and well-organized. With the multiple types of drug materials of large dosages, efficacies of the various drug materials generate a synergistic effect, with the functions of resolving depression promoting the circulation of qi, and the qi depression constitution can be corrected, so that people are vigorous with strong resistibility, and the occurrence of diseases is avoided. With the correction for such constitution, it is more targeted and will not create side effects, without harm to the human body at all, and can achieve certain efficacy of strengthening the body.

Figure 1:
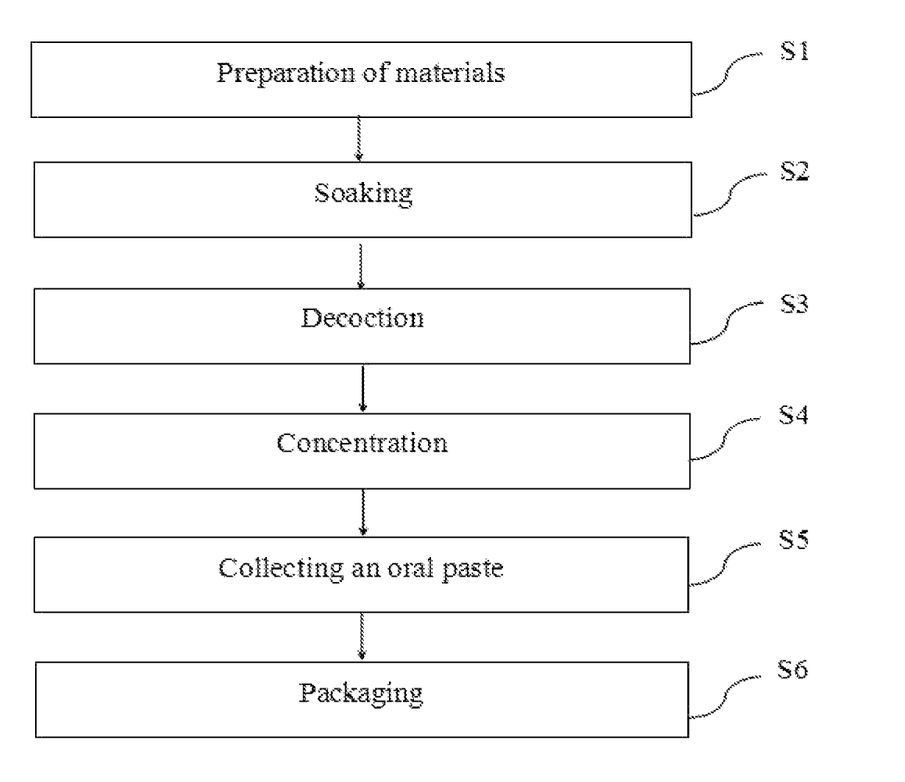
FIG. 1 is a flow chart of a processing technology for a Chinese herbal oral paste of an embodiment of the present disclosure.

As shown in FIG. 1, the processing method for the Chinese herbal oral paste for conditioning qi depression constitution of the present disclosure includes the following steps in sequence: preparation of materials, soaking, decoction, concentration, collecting an oral paste, and finally packaging. For specific operations of respective steps, reference can be made to various embodiments of the present disclosure.

Embodiment 1:

A Chinese herbal oral paste for conditioning qi depression constitution includes the following components in parts by weight: 9 parts of Chinese thorowax root, 5 parts of debark peony root, 2 parts of licorice, 2 parts of Sichuan lovage rhizome, 4 parts of dried tangerine peel, 5 parts of orange fruit, 3 parts of nutgrass galingale rhizome, 5 parts of mint, 5 parts of fuling, 4 parts of perilla leaf, 5 parts of largehead atractylodes rhizome, 12 parts of fruit of caoguo, 5 parts of common aucklandia root, 5 parts of chinaberry fruit, 6 parts of lychee seed, 5 parts of finger citron, 5 parts of citron fruit, 6 parts of rose flower, 3 parts of citrus aurantium L, 4 parts of silktree albizia bark, 5 parts of nardostachys root, 4 parts of grassleaf sweetflag rhizome, 8 parts of heterophylly falsestarwort root, 5 parts of Chinese yam, 5 parts of white hyacinth bean, 4 parts of dendrobium, 6 parts of turmeric root tuber, 10 parts of donkey-hide gelatin, 5 parts of turtle shell gelatin, 5 parts of tortoise-plastron gelatin, and 20 parts of xylitol.

The processing method therefor includes the following steps in sequence:

preparation of materials: measuring raw materials of formula ratio according to composition of the Chinese herbal oral paste, and washing raw materials, except turtle shell gelatin, tortoise-plastron gelatin, donkey-hide gelatin, and xylitol, for subsequent use;

soaking: soaking the cleaned raw materials with 8 folds of water for 8 h, with the water over the raw materials by 10 cm;

decoction: decocting the soaked drug materials over flame, firstly boiling the drug materials with high heat to sufficiently expand, then boiling the drug materials with low heat for 1 hour of decoction, then filtering drug juice with gauze, then soaking filtered dregs of decoction with clear water and decocting the soaked dregs of decoction with low heat for 1 hour, thus repeating 4 times, then combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol, melted turtle shell gelatin, tortoise-plastron gelatin and donkey-hide gelatin into the vegetarian paste respectively, stirring them continuously with a shovel and cooking them slowly with low heat, until the juice can coagulate into beads and not disperse when being dropped into clear water, then canning the resulted oral paste.

In the above, the step of melting gelatin type drugs is: smashing lumps of turtle shell gelatin, tortoise-plastron gelatin and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 2:

A Chinese herbal oral paste for conditioning qi depression constitution includes the following components in parts by weight: 18 parts of Chinese thorowax root, 15 parts of debark peony root, 11 parts of licorice, 10 parts of Sichuan lovage rhizome, 16 parts of dried tangerine peel, 16 parts of orange fruit, 8 parts of nutgrass galingale rhizome, 15 parts of mint, 16 parts of fuling, 14 parts of perilla leaf, 16 parts of largehead atractylodes rhizome, 28 parts of fruit of caoguo, 15 parts of common aucklandia root, 16 parts of chinaberry fruit, 18 parts of lychee seed, 14 parts of finger citron, 16 parts of citron fruit, 16 parts of rose flower, 10 parts of citrus aurantium L, 15 parts of silktree albizia bark, 16 parts of nardostachys root, 9 parts of grassleaf sweetflag rhizome, 22 parts of heterophylly falsestarwort root, 15 parts of Chinese yam, 15 parts of white hyacinth bean, 17 parts of dendrobium, 18 parts of turmeric root tuber, 30 parts of donkey-hide gelatin, 15 parts of turtle shell gelatin, 15 parts of tortoise-plastron gelatin, and 40 parts of xylitol.

The processing method therefor includes the following steps in sequence:

preparation of materials: measuring raw materials of formula ratio according to composition of the Chinese herbal oral paste, and washing raw materials, except turtle shell gelatin, tortoise-plastron gelatin, donkey-hide gelatin, and xylitol, for subsequent use;

soaking: soaking the cleaned raw materials with 10 folds of water for 15 h, with the water over the raw materials by 20 cm;

decoction: decocting the soaked drug materials over flame, firstly boiling the drug materials with high heat to sufficiently expand, then boiling the drug materials with low heat for 2 hours of decoction, then filtering drug juice with gauze, then soaking filtered dregs of decoction with clear water and decocting the soaked dregs of decoction with low heat for 1 hour, thus repeating 2 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol, melted turtle shell gelatin, tortoise-plastron gelatin and donkey-hide gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of turtle shell gelatin, tortoise-plastron gelatin and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 3:

A Chinese herbal oral paste for conditioning qi depression constitution includes the following components in parts by weight: 9 parts of Chinese thorowax root, 7 parts of debark peony root, 4 parts of licorice, 4 parts of Sichuan lovage rhizome, 7 parts of dried tangerine peel, 7 parts of orange fruit, 5 parts of nutgrass galingale rhizome, 7 parts of mint, 7 parts of fuling, 7 parts of perilla leaf, 7 parts of largehead atractylodes rhizome, 16 parts of fruit of caoguo, 7 parts of common aucklandia root, 8 parts of chinaberry fruit, 9 parts of lychee seed, 7 parts of finger citron, 7 parts of citron fruit, 8 parts of rose flower, 5 parts of citrus aurantium L, 7 parts of silktree albizia bark, 7 parts of nardostachys root, 5 parts of grassleaf sweetflag rhizome, 11 parts of heterophylly falsestarwort root, 7 parts of Chinese yam, 7 parts of white hyacinth bean, 7 parts of dendrobium, 9 parts of turmeric root tuber, 15 parts of donkey-hide gelatin, 7 parts of turtle shell gelatin, 7 parts of tortoise-plastron gelatin, and 25 parts of xylitol.

The processing method therefor includes the following steps in sequence:

preparation of materials: measuring raw materials of formula ratio according to composition of the Chinese herbal oral paste, and washing raw materials, except turtle shell gelatin, tortoise-plastron gelatin, donkey-hide gelatin, and xylitol, for subsequent use;

soaking: soaking the cleaned raw materials with 9 folds of water for 10 h, with the water over the raw materials by 13 cm;

decoction: decocting the soaked drug materials over flame, firstly boiling the drug materials with high heat to sufficiently expand, then boiling the drug materials with low heat for 1.5 hours of decoction, then filtering drug juice with gauze, then soaking filtered dregs of decoction with clear water and decocting the soaked dregs of decoction with low heat for 1 hour, thus repeated 3 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol, and melted turtle shell gelatin, tortoise-plastron gelatin and donkey-hide gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of turtle shell gelatin, tortoise-plastron gelatin and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 4:

A Chinese herbal oral paste for conditioning qi depression constitution includes the following components in parts by weight: 15 parts of Chinese thorowax root, 13 parts of debark peony root, 8 parts of licorice, 8 parts of Sichuan lovage rhizome, 13 parts of dried tangerine peel, 13 parts of orange fruit, 7 parts of nutgrass galingale rhizome, 13 parts of mint, 13 parts of fuling, 13 parts of perilla leaf, 13 parts of largehead atractylodes rhizome, 24 parts of fruit of caoguo, 13 parts of common aucklandia root, 13 parts of chinaberry fruit, 15 parts of lychee seed, 12 parts of finger citron, 13 parts of citron fruit, 13 parts of rose flower, 7 parts of citrus aurantium L, 13 parts of silktree albizia bark, 13 parts of nardostachys root, 7 parts of grassleaf sweetflag rhizome, 19 parts of heterophylly falsestarwort root, 13 parts of Chinese yam, 13 parts of white hyacinth bean, 13 parts of dendrobium, 15 parts of turmeric root tuber, 25 parts of donkey-hide gelatin, 13 parts of turtle shell gelatin, 13 parts of tortoise-plastron gelatin, and 35 parts of xylitol.

The processing method therefor includes the following steps in sequence:

preparation of materials: measuring raw materials of formula ratio according to composition of the Chinese herbal oral paste, and washing raw materials, except turtle shell gelatin, tortoise-plastron gelatin, donkey-hide gelatin, and xylitol, for subsequent use;

soaking: soaking the cleaned raw materials with 9 folds of water for 11 h, with the water over the raw materials by 15 cm;

decoction: decocting the soaked drug materials over flame, firstly boiling the drug materials with high heat to sufficiently expand, then boiling the drug materials with low heat for 1.5 hours of decoction, then filtering drug juice with gauze, then soaking filtered dregs of decoction with clear water and decocting the soaked dregs of decoction with low heat for 1 hour, thus repeated 3 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol, melted turtle shell gelatin, tortoise-plastron gelatin and donkey-hide gelatin into the vegetarian paste respectively, stirring them continuously with a shovel and cooking them slowly with low heat, until the juice can coagulate into beads and not disperse when being dropped into clear water, then canning the resulted oral paste.

In the above, the step of melting gelatin type drugs is: smashing lumps of turtle shell gelatin, tortoise-plastron gelatin and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 5:

A Chinese herbal oral paste for conditioning qi depression constitution includes the following components in parts by weight: 12 parts of Chinese thorowax root, 10 parts of debark peony root, 6 parts of licorice, 6 parts of Sichuan lovage rhizome, 10 parts of dried tangerine peel, 10 parts of orange fruit, 6 parts of nutgrass galingale rhizome, 10 parts of mint, 10 parts of fuling, 10 parts of perilla leaf, 10 parts of largehead atractylodes rhizome, 20 parts of fruit of caoguo, 10 parts of common aucklandia root, 10 parts of chinaberry fruit, 12 parts of lychee seed, 10 parts of finger citron, 10 parts of citron fruit, 10 parts of rose flower, 6 parts of citrus aurantium L, 10 parts of silktree albizia bark, 10 parts of nardostachys root, 6 parts of grassleaf sweetflag rhizome, 15 parts of heterophylly falsestarwort root, 10 parts of Chinese yam, 10 parts of white hyacinth bean, 10 parts of dendrobium, 12 parts of turmeric root tuber, 20 parts of donkey-hide gelatin, 10 parts of turtle shell gelatin, 10 parts of tortoise-plastron gelatin, and 30 parts of xylitol.

The processing method therefor includes the following steps in sequence:

preparation of materials: measuring raw materials of formula ratio according to composition of the Chinese herbal oral paste, and washing raw materials, except turtle shell gelatin, tortoise-plastron gelatin, donkey-hide gelatin, and xylitol, for subsequent use;

soaking: soaking the cleaned raw materials with 9 folds of water for 12 h, with the water over the raw materials by 17 cm;

decoction: decocting the soaked drug materials over flame, firstly boiling the drug materials with high heat to sufficiently expand, then boiling the drug materials with low heat for 1.5 hours of decoction, then filtering drug juice with gauze, then soaking filtered dregs of decoction with clear water and decocting the soaked dregs of decoction with low heat for 1 hour, thus repeating 3 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring and decocting and concentrating with low heat, until a drug liquid does not disperse when being dropped on paper, to obtain a vegetarian paste;

collecting an oral paste: pouring xylitol, melted turtle shell gelatin, tortoise-plastron gelatin and donkey-hide gelatin into the vegetarian paste respectively, stirring them continuously with a shovel while cooking them slowly with low heat, until the juice can coagulate into beads and does not disperse when being dropped into clear water, then canning the resulted oral paste.

In the above, the step of melting gelatin type drugs is: smashing lumps of turtle shell gelatin, tortoise-plastron gelatin and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

EXPERIMENT EXAMPLE 1

250 volunteers with the qi depression constitution were recruited, and equally divided into 5 groups to respectively use the Chinese herbal oral paste prepared according to Embodiments 1 to 5 for conducting the treatment experiment. Usage: 25 g each time, once a day. Brew 25 g of the oral paste with boiling water in a cup, and stir the oral paste to make it melt for administration. After one month of drinking, the qi depression status of their constitution was assessed, and the final treatment effects were evaluated into three types: cured, effective, and ineffective, among which, "cured" refers to that the qi depression constitution is significantly improved, and the qi depression symptoms basically completely disappear; "effective" refers to that the qi depression constitution is effectively improved, and the qi depression symptoms partially disappear; "ineffective" refers to that the qi depression constitution is basically not improved, and almost none of the symptoms caused by qi depression disappears. The statistics results of the volunteers evaluated are shown in the following Table 1.

TABLE 1

Treatment Effects of Volunteers with Qi Depression Constitution

| Embodiment | Cured/Person | Effective/Person | Ineffective/Person | Effective Rate/% |
|---|---|---|---|---|
| 1 | 41 | 6 | 3 | 94 |
| 2 | 38 | 7 | 5 | 90 |
| 3 | 43 | 6 | 1 | 98 |
| 4 | 42 | 3 | 5 | 90 |
| 5 | 46 | 4 | 0 | 100 |
| Total | 210 | 26 | 14 | 94.4 |

EXPERIMENT EXAMPLE 2

Animal Toxicity Test

1. Animal Acute Toxicity Test of the Chinese Herbal Oral Paste of the Present Disclosure Supply: the Chinese herbal oral paste prepared according to Embodiment 5 of the present disclosure.

Acute toxicity: 30 mice of 18-22 g were selected, and were administrated once by gavage according to the dosage of 0.4 g/kg. No mouse died after continual observation of 3 days. Subacute toxicity test was also conducted in the present experiment. Results show that after the administration of the Chinese herbal oral paste particles of Embodiment 5 according to the above dosage, no significant abnormality was observed in various examination indexes and pathological tissue sections.

2. Animal Long-term Toxicity Test of the Chinese Herbal Oral Paste of the Present Disclosure:

Test objective: observe toxic reactions generated by rats after 3 months of continual administration of the Chinese herbal oral paste of the present disclosure by gavage, so as to ensure usage safety.

Supply: the Chinese herbal oral paste prepared according to Embodiment 5 of the present disclosure.

Test animals: Wister rats, half males and half females, with a mean body weight of 100±8.87 g for the males, and a mean body weight of 110±9.74 g for the females.

Test method: the test animals were randomly divided into three groups: a control group; a group of high-dosage 0.6 g/kg of the Chinese herbal oral paste; a group of low-dosage 0.3 g/kg of the Chinese herbal oral paste. Each group had 20 rats, half males and half females, and the administration by gavage was made according to the dosage every day; the control group was fed with drinking water of the same weight. The administration and feeding were continued for 12 weeks.

The general states of the animals were observed during the administration, and they were weighed every week. On the next day of drug withdrawal, the animals of respective groups were subjected to intraperitoneal injection of 30 mg/kg of pentobarbital sodium to anaesthetize, and blood was taken from the ventral abdominal artery to measure various indexes of the blood; the serum was segregated to conduct liver and kidney function tests. The main internal organs of the rats were taken out and weighed, and the organ coefficient was calculated according to the weights, meanwhile, visual inspection and microscopic pathological examination, etc. were conducted on the same. The remaining half of the animals stopped taking the drug, and were continuously fed for two weeks to observe changes in the recovery phase.

Test Results: (1) general state: the rats of the two dosage groups were normal in activity during the administration, with no significant abnormality in food-intake, water drinking, or defecation, and without death; (2) body weight: the rats of the two dosage groups did not have significant differences in the growth and change of the body weight from the control group during the administration and recovery phase; (3) hematology examination: after 12 weeks of administration of the two dosage groups, all the various indexes measured are within normal ranges, without remarkable difference from the control group; (4) serum biochemical examination: after 12 weeks of continuous administration of the two dosage groups, all the various biochemical indexes are within normal ranges, without remarkable difference from the control group; (5) histological observation: the rats of the two dosage groups and the control group were subjected to autopsy after the end of the administration period, and upon visual observation and tissue section observation, no significant pathological change was observed.

Test conclusion: after 12 weeks of administration of the Chinese herbal oral paste by gavage for the rats of the two groups—the high-dosage group and the low-dosage group, no growth is observed in the animals' appearance or body weight; the toxicity changes in the hematology, serum biochemistry, and the main internal organs indicate that the Chinese herbal oral paste particles of the present disclosure have no significant toxic effect within the used dosages and administration period.

It should be indicated that Embodiments 1-5 of the present invention are merely some of the embodiments for implementing the technical solutions of the present invention, and should not be construed as the scope of protection of the present invention merely limited to the above five embodiments, and a person skilled in the art can make further improvements on the basis of the present invention without departing from the principle and spirit of the present invention.

For example, the components of the Chinese herbal oral paste of the present invention are not limited to those listed in respective embodiments, while other Chinese herbal medicines also can be added, to further perfecting the drug formulation of the Chinese herbal oral paste of the present invention.

For another example, in the process of the processing method for the Chinese herbal oral paste of the present invention, in the concentration step, when the drug juice is concentrated to the vegetarian paste, a wild jujube shell powder is added evenly with stirring. The wild jujube shell powder above is obtained by sufficiently smashing and grinding the wild jujube shell, with a particle size of 100-400 micrometers. The wild jujube shell powder has the main components of cellulose and lignin, has quite advanced pores in the powder particles, and is a natural drug carrier. When added to the Chinese herbal oral paste, the pores inside the wild jujube shell powder will be filled up with the drug components of the Chinese herbal oral paste. Since the cellulose and lignin cannot be digested or absorbed in vivo, they can be effective as sustained release, then a small part of the drug components stored in the wild jujube shell powder can be released continuously, so that the drug is present in the digestive system for an extended period of time. The phenomenon that the drug components are wasted as the digestive system cannot absorb a large amount of drug components within a short period of time will not occur. The wild jujube shell powder is added in an amount of 1%-3% of the gelatin type drugs, and should not be used in an excessive amount, because the excessive amount, on one hand, will deteriorate the form quality of the oral paste, and on the other hand, will increase the burdens of the intestines and stomach as it cannot be absorbed by the human body.

The descriptions above are only preferred embodiments of the present invention, which are not used to limit the present invention. For a person skilled in the art, the present invention may have various changes and variations. Any modifications, equivalent substitutions, improvements etc. within the spirit and principle of the present invention shall all be included in the scope of protection of the present invention.

What is claimed is:

1. A Chinese herbal oral paste for conditioning qi depression constitution, comprising the following components in parts by weight: 9-18 parts of Chinese thorowax root, 5-15 parts of debarked peony root, 2-11 parts of licorice, 2-10 parts of Sichuan lovage rhizome, 4-16 parts of dried tangerine peel, 5-16 parts of orange fruit, 3-8 parts of nutgrass galingale rhizome, 5-15 parts of mint, 5-16 parts of fuling, 4-14 parts of perilla leaf, 5-16 parts of largehead atractylodes rhizome, 12-28 parts of fruit of caoguo, 5-15 parts of common aucklandia root, 5-16 parts of chinaberry fruit, 6-18 parts of lychee seed, 5-14 parts of finger citron, 5-16 parts of citron fruit, 6-16 parts of rose flower, 3-10 parts of citrus aurantium L, 4-15 parts of silktree albizia bark, 5-16 parts of nardostachys root, 4-9 parts of grassleaf sweetflag rhizome, 8-22 parts of heterophylly falsestarwort root, 5-15 parts of Chinese yam, 5-15 parts of white hyacinth bean, 4-17 parts of dendrobium, 6-18 parts of turmeric root tuber, 10-30 parts of donkey-hide gelatin, 5-15 parts of turtle shell gelatin, 5-15 parts of tortoise-plastron gelatin, and 20-40 parts of xylitol.

2. The Chinese herbal oral paste for conditioning qi depression constitution of claim 1, wherein the Chinese thorowax root is 9-15 parts by weight, the debarked peony root is 7-13 parts by weight, the licorice is 4-8 parts by weight, the Sichuan lovage rhizome is 4-8 parts by weight, the dried tangerine peel is 7-13 parts by weight, the orange fruit is 7-13 parts by weight, the nutgrass galingale rhizome is 5-7 parts by weight, the mint is 7-13 parts by weight, the fuling is 7-13 parts by weight, the perilla leaf is 7-13 parts by weight, the largehead atractylodes rhizome is 7-13 parts by weight, the fruit of caoguo is 16-24 parts by weight, the common aucklandia root is 7-13 parts by weight, the chinaberry fruit is 8-13 parts by weight, the lychee seed is 9-15 parts by weight, the finger citron is 7-12 parts by weight, the citron fruit is 7-13 parts by weight, the rose flower is 8-13 parts by weight, the citrus aurantium L is 5-7 parts by weight, the silktree albizia bark is 7-13 parts by weight, the nardostachys root is 7-13 parts by weight, the grassleaf sweetflag rhizome is 5-7 parts by weight, the heterophylly falsestarwort root is 11-19 parts by weight, the Chinese yam is 7-13 parts by weight, the white hyacinth bean is 7-13 parts by weight, the dendrobium is 7-13 parts by weight, the turmeric root tuber is 9-15 parts by weight, the donkey-hide gelatin is 15-25 parts by weight, the turtle shell gelatin is 7-13 parts by weight, the tortoise-plastron gelatin is 7-13 parts by weight, and the xylitol is 25-35 parts by weight.

3. The Chinese herbal oral paste for conditioning qi depression constitution of claim 1, wherein the Chinese thorowax root is 12 parts by weight, the debarked peony root is 10 parts by weight, the licorice is 6 parts by weight, the Sichuan lovage rhizome is 6 parts by weight, the dried tangerine peel is 10 parts by weight, the orange fruit is 10 parts by weight, the nutgrass galingale rhizome is 6 parts by weight, the mint is 10 parts by weight, the fuling is 10 parts by weight, the perilla leaf is 10 parts by weight, the largehead atractylodes rhizome is 10 parts by weight, the fruit of caoguo is 20 parts by weight, the common aucklandia root is 10 parts by weight, the chinaberry fruit is 10 parts by weight, the lychee seed is 12 parts by weight, the finger citron is 10 parts by weight, the citron fruit is 10 parts by weight, the rose flower is 10 parts by weight, the citrus aurantium L is 6 parts by weight, the silktree albizia bark is 10 parts by weight, the nardostachys root is 10 parts by weight, the grassleaf sweetflag rhizome is 6 parts by weight, the heterophylly falsestarwort root is 15 parts by weight, the Chinese yam is 10 parts by weight, the white hyacinth bean is 10 parts by weight, the dendrobium is 10 parts by weight, the turmeric root tuber is 12 parts by weight, the donkey-hide gelatin is 20 parts by weight, the turtle shell gelatin is 10 parts by weight, the tortoise-plastron gelatin is 10 parts by weight, and the xylitol is 30 parts by weight.

4. A processing method for the Chinese herbal oral paste for conditioning qi depression constitution of claim 1, comprising the following steps in sequence: preparation of materials, soaking, decoction, concentration, and collecting an oral paste.

5. The processing method for the Chinese herbal oral paste for conditioning qi depression constitution of claim 4, wherein the step of preparation of materials is: measuring raw materials of formula ratio according to composition of the Chinese herbal oral paste, and washing raw materials, except turtle shell gelatin, tortoise-plastron gelatin, donkey-hide gelatin, and xylitol, for subsequent use.

6. The processing method for the Chinese herbal oral paste for conditioning qi depression constitution of claim 5, wherein the soaking step is: soaking the cleaned raw materials with 8-10 folds of water for 8-15 h, with the water over the raw materials by 10-20 cm.

7. The processing method for the Chinese herbal oral paste for conditioning qi depression constitution of claim 6, wherein the decoction step is: decocting the soaked drug materials over flame, firstly boiling the drug materials with high heat to sufficiently expand, then boiling the drug materials with low heat for 1-2 hours of decoction, then filtering drug juice with gauze, then soaking filtered dregs of decoction with clear water and decocting the soaked dregs of decoction with low heat for 1 hour, thus repeating 2-4 times, then combining the filtered drug juice, and squeezing and filtering the dregs to obtain a squeezed juice; combining the decoction juice with the squeezed juice, followed by static settlement for 2 h, and filtering, to obtain a supernatant liquid for subsequent use.

8. The processing method for the Chinese herbal oral paste for conditioning qi depression constitution of claim 7, wherein the concentration step is: boiling and skimming the supernatant liquid resulted in the decoction step, followed by stirring while decocting and concentrating with low heat, until a drug liquid does not disperse when being dropped on paper, to obtain a vegetarian paste.

9. The processing method for the Chinese herbal oral paste for conditioning qi depression constitution of claim 8, wherein the step of collecting an oral paste is: pouring xylitol, and melted turtle shell gelatin, tortoise-plastron gelatin and donkey-hide gelatin into the vegetarian paste respectively, stirring them continuously with a shovel while cooking them slowly with low heat, until the juice can coagulate into beads and not disperse when being dropped into clear water, then canning the resulted oral paste.

10. The processing method for the Chinese herbal oral paste for conditioning qi depression constitution of claim 9, wherein the melting step is: smashing lumps of turtle shell gelatin, tortoise-plastron gelatin and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

11. A processing method for the Chinese herbal oral paste for conditioning qi depression constitution of claim 2, comprising the following steps in sequence: preparation of materials, soaking, decoction, concentration, and collecting an oral paste.

12. The processing method for the Chinese herbal oral paste for conditioning qi depression constitution of claim 11, wherein the step of preparation of materials is: measuring raw materials of formula ratio according to composition of the Chinese herbal oral paste, and washing raw materials, except turtle shell gelatin, tortoise-plastron gelatin, donkey-hide gelatin, and xylitol, for subsequent use.

13. The processing method for the Chinese herbal oral paste for conditioning qi depression constitution of claim 12, wherein the soaking step is: soaking the cleaned raw materials with 8-10 folds of water for 8-15 h, with the water over the raw materials by 10-20 cm.

14. The processing method for the Chinese herbal oral paste for conditioning qi depression constitution of claim 13, wherein the decoction step is: decocting the soaked drug materials over flame, firstly boiling the drug materials with high heat to sufficiently expand, then boiling the drug materials with low heat for 1-2 hours of decoction, then filtering drug juice with gauze, then soaking filtered dregs of decoction with clear water and decocting the soaked dregs of decoction with low heat for 1 hour, thus repeating 2-4 times, then combining the filtered drug juice, and squeezing and filtering the dregs to obtain a squeezed juice; combining the decoction juice with the squeezed juice, followed by static settlement for 2 h, and filtering, to obtain a supernatant liquid for subsequent use.

15. The processing method for the Chinese herbal oral paste for conditioning qi depression constitution of claim 14, wherein the concentration step is: boiling and skimming the supernatant liquid resulted in the decoction step, followed by stirring while decocting and concentrating with low heat, until a drug liquid does not disperse when being dropped on paper, to obtain a vegetarian paste.

16. The processing method for the Chinese herbal oral paste for conditioning qi depression constitution of claim 15, wherein the step of collecting an oral paste is: pouring xylitol, and melted turtle shell gelatin, tortoise-plastron gelatin and donkey-hide gelatin into the vegetarian paste respectively, stirring them continuously with a shovel while cooking them slowly with low heat, until the juice can coagulate into beads and not disperse when being dropped into clear water, then canning the resulted oral paste.

17. The processing method for the Chinese herbal oral paste for conditioning qi depression constitution of claim 16, wherein the melting step is: smashing lumps of turtle shell gelatin, tortoise-plastron gelatin and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

18. A processing method for the Chinese herbal oral paste for conditioning qi depression constitution of claim 3, comprising the following steps in sequence: preparation of materials, soaking, decoction, concentration, and collecting an oral paste.

19. The processing method for the Chinese herbal oral paste for conditioning qi depression constitution of claim 18, wherein the step of preparation of materials is: measuring raw materials of formula ratio according to composition of the Chinese herbal oral paste, and washing raw materials, except turtle shell gelatin, tortoise-plastron gelatin, donkey-hide gelatin, and xylitol, for subsequent use.

20. The processing method for the Chinese herbal oral paste for conditioning qi depression constitution of claim 19, wherein the soaking step is: soaking the cleaned raw materials with 8-10 folds of water for 8-15 h, with the water over the raw materials by 10-20 cm.

* * * * *